(12) United States Patent
Allen (10) Patent No.: US 10,271,916 B2
(45) Date of Patent: Apr. 30, 2019

(54) ZIP STRIP DRAPING SYSTEM AND METHODS OF MANUFACTURING SAME

(75) Inventor: Fred L. Allen, Wonder Lake, IL (US)

(73) Assignee: Medline Industries, Inc., Mundelein, IL (US)

( * ) Notice: Subject to any disclaimer, the term of this patent is extended or adjusted under 35 U.S.C. 154(b) by 974 days.

(21) Appl. No.: 12/188,931

(22) Filed: Aug. 8, 2008

(65) Prior Publication Data

US 2010/0031966 A1    Feb. 11, 2010

(51) Int. Cl.
*A61F 5/37* (2006.01)
*A61B 46/00* (2016.01)
*A61B 17/00* (2006.01)

(52) U.S. Cl.
CPC .... *A61B 46/00* (2016.02); *A61B 2017/00526* (2013.01)

(58) Field of Classification Search
CPC ............................ A61B 19/08; A61B 2019/08
USPC ........................................ 128/853, 849, 851
See application file for complete search history.

(56) References Cited

U.S. PATENT DOCUMENTS

| 371,353 | A | 10/1887 | Perry |
| 850,960 | A | 4/1907 | O'Connoor |
| 936,383 | A | 10/1909 | Thibodeau |
| 1,506,332 | A | 8/1924 | Bloom |
| 1,980,435 | A | 11/1934 | Reagan |
| 2,172,162 | A | 8/1939 | Gillette |
| 2,430,941 | A | 11/1947 | Long |
| 2,653,324 | A | 8/1953 | McMahon |
| 2,673,347 | A | 3/1954 | Weiss |
| 3,130,462 | A | 4/1964 | Mitchell |
| 3,276,036 | A | 10/1966 | Carter et al. |
| 3,397,406 | A | 8/1968 | Leach |
| 3,399,406 | A | 9/1968 | Bradley |
| 3,451,062 | A | 6/1969 | Bradley |
| 3,696,443 | A | 10/1972 | Taylor |

(Continued)

FOREIGN PATENT DOCUMENTS

| DE | 89 04 426 U1 | 5/1989 | ............. A61B 19/08 |
| DE | 20 2006 005 996 U1 | 10/2006 | ............. A61F 13/15 |

(Continued)

OTHER PUBLICATIONS

Canadian Office Action for Canadian Patent No. 2,674,951 dated May 4, 2011 (3 pages).

(Continued)

*Primary Examiner* — Victoria J Hicks
(74) *Attorney, Agent, or Firm* — Nixon Peabody LLP (57) ABSTRACT

A medical drape has a tool-less removal feature and includes a drape material, a drape cut, an adhesive tape strip, and a scoreline. The drape material has a top side, a back side, and at least one exterior edge. The drape cut has a starting point at the exterior edge and extends completely through the thickness of the drape material. The adhesive tape strip is positioned along the length of the drape cut to overlap at least a portion of the drape material on both sides of the drape cut to initially secure the two adjoining cut edges to each other. The scoreline extends along the length of the adhesive tape strip and only partially through the thickness of the adhesive tape strip to permit easy tearing of the adhesive tape strip for separation of the two adjoining cut edges.

9 Claims, 4 Drawing Sheets

(56) References Cited

U.S. PATENT DOCUMENTS

| | | | |
|---|---|---|---|
| 3,707,964 A | 1/1973 | Patience et al. | |
| 3,750,664 A | 8/1973 | Collins | 128/132 D |
| 3,803,640 A | 4/1974 | Ericson | |
| 3,881,474 A | 5/1975 | Krzewinski | 128/132 D |
| 3,881,476 A | 5/1975 | Bolker et al. | |
| 3,952,373 A | 4/1976 | Noorily | |
| 3,956,048 A | 5/1976 | Nordgren | 156/183 |
| 3,968,792 A | 7/1976 | Small | |
| 3,989,040 A | 11/1976 | Lofgren et al. | |
| 4,017,909 A | 4/1977 | Brandriff | |
| 4,041,942 A | 8/1977 | Dougan et al. | 128/132 D |
| 4,119,093 A | 10/1978 | Goodman | |
| 4,134,398 A | 1/1979 | Scrivens | 128/132 D |
| 4,153,054 A | 5/1979 | Boone | |
| 4,266,663 A | 5/1981 | Geraci | 206/223 |
| 4,290,148 A | 8/1981 | Roberts | |
| 4,308,864 A | 1/1982 | Small et al. | |
| 4,323,062 A | 4/1982 | Canty | 128/132 D |
| 4,334,529 A | 5/1982 | Wirth | 128/132 D |
| 4,384,573 A | 5/1983 | Elliott | |
| 4,476,860 A | 10/1984 | Collins et al. | |
| 4,479,492 A | 10/1984 | Singer | |
| 4,489,720 A | 12/1984 | Morris et al. | 128/132 D |
| 4,553,538 A | 11/1985 | Rafelson | 128/132 D |
| 4,569,341 A | 2/1986 | Morris | |
| 4,596,245 A | 6/1986 | Morris | 128/132 D |
| 4,616,642 A | 10/1986 | Martin et al. | 128/132 D |
| 4,627,427 A | 12/1986 | Acro | |
| 4,664,103 A | 5/1987 | Martin et al. | 128/132 D |
| 4,711,236 A | 12/1987 | Glassman | 128/132 |
| 4,745,915 A | 5/1988 | Enright et al. | 128/132 |
| 4,829,602 A | 5/1989 | Harreld et al. | |
| 4,869,271 A | 9/1989 | Idris | 128/853 |
| 4,905,710 A | 3/1990 | Jones | |
| 4,920,578 A | 5/1990 | Janzen et al. | |
| 4,951,318 A | 8/1990 | Harreld et al. | |
| 5,042,507 A | 8/1991 | Dowdy | |
| 5,061,246 A | 10/1991 | Anapliotis | |
| 5,074,316 A | 12/1991 | Dowdy | |
| 5,109,873 A * | 5/1992 | Marshall | A61B 19/08 128/849 |
| 5,135,188 A | 8/1992 | Anderson et al. | |
| 5,136,758 A | 8/1992 | Wilcox et al. | |
| 5,140,996 A | 8/1992 | Sommers et al. | 128/849 |
| 5,362,306 A | 11/1994 | McCarver et al. | |
| 5,372,589 A | 12/1994 | Davis | |
| 5,377,387 A | 1/1995 | Freed | |
| D356,204 S | 3/1995 | Derrickson | |
| 5,410,758 A | 5/1995 | Dupont et al. | |
| 5,414,867 A | 5/1995 | Bowling et al. | |
| 5,417,225 A * | 5/1995 | Rubenstein | A61B 19/40 128/849 |
| 5,444,873 A | 8/1995 | Levin | |
| 5,605,534 A | 2/1997 | Hutchison | |
| 5,611,356 A | 3/1997 | Rothrum | |
| 5,674,189 A | 10/1997 | McDowell et al. | |
| 5,707,703 A | 1/1998 | Rothrum et al. | |
| 5,765,566 A | 6/1998 | Rothrum | |
| 5,778,889 A | 7/1998 | Jascomb | |
| 5,816,253 A | 10/1998 | Sosabee | 128/849 |
| 5,916,202 A | 6/1999 | Haswell | |
| 5,973,450 A | 10/1999 | Nishizawa et al. | 313/478 |
| 5,975,082 A | 11/1999 | Dowdy | |
| 5,985,395 A | 11/1999 | Comstock et al. | |
| 6,049,907 A | 4/2000 | Palomo | |
| 6,105,579 A | 8/2000 | Levitt et al. | 128/849 |
| 6,115,840 A | 9/2000 | Hastins | |
| 6,138,278 A | 10/2000 | Taylor | |
| 6,196,033 B1 | 3/2001 | Dowdle | |
| 6,216,270 B1 | 4/2001 | Moquin et al. | |
| 6,244,268 B1 | 6/2001 | Annett | 128/849 |
| 6,272,685 B1 | 8/2001 | Kumar | |
| 6,285,611 B1 | 9/2001 | Kang | 365/205 |
| 6,345,622 B1 | 2/2002 | Chandler et al. | 128/849 |
| 6,405,730 B2 | 6/2002 | Levitt et al. | 128/849 |
| 6,378,136 B2 | 8/2002 | Matsushita | |
| 6,536,636 B1 | 3/2003 | McDonniel | |
| 6,564,386 B2 | 5/2003 | Fujikawa et al. | |
| 6,694,981 B2 | 2/2004 | Gingles et al. | |
| 6,742,522 B1 | 6/2004 | Baker et al. | 128/849 |
| 6,820,622 B1 | 11/2004 | Teves et al. | 128/849 |
| 6,843,252 B2 | 1/2005 | Harrison et al. | 128/849 |
| 7,114,500 B2 | 10/2006 | Bonutti | |
| D533,982 S | 12/2006 | Graneto, III | |
| 7,181,773 B1 | 2/2007 | Piraka | |
| 7,237,271 B1 | 7/2007 | McLandrich | |
| 7,290,547 B2 | 11/2007 | Joseph et al. | |
| 7,305,991 B2 | 12/2007 | Santilli et al. | 128/849 |
| D579,178 S | 10/2008 | Snyder et al. | |
| 7,454,798 B2 | 11/2008 | Feodoroff | |
| 7,549,179 B1 | 6/2009 | Saied | |
| D598,638 S | 8/2009 | Graneto, III | |
| 7,654,266 B2 | 2/2010 | Corbitt, Jr. | |
| D622,479 S | 8/2010 | Herzog | |
| D622,934 S | 9/2010 | Graneto, III | |
| 7,971,274 B2 | 7/2011 | Graneto, III | |
| 8,141,172 B2 | 3/2012 | Furlong | |
| 8,343,182 B2 | 1/2013 | Kirkham | |
| 8,375,466 B2 | 2/2013 | Tasezen | |
| 2002/0095709 A1 | 7/2002 | Fujikawa et al. | |
| 2003/0121522 A1 | 7/2003 | Gingles et al. | |
| 2004/0103904 A1 | 6/2004 | Auerbach et al. | |
| 2005/0145254 A1 | 7/2005 | Aboul-Hosn et al. | 128/852 |
| 2005/0223468 A1 | 10/2005 | Hatton | |
| 2005/0279366 A1 | 12/2005 | Adragna | |
| 2006/0000002 A1 | 1/2006 | Bergkvist | |
| 2006/0081261 A1 | 4/2006 | Corbitt, Jr. | 128/849 |
| 2006/0117452 A1 | 6/2006 | Ambrose | |
| 2006/0191541 A1 | 8/2006 | Aboul-Hosn et al. | 128/849 |
| 2007/0102005 A1 | 5/2007 | Bonutti | 128/849 |
| 2007/0083032 A1 | 7/2007 | Carrez et al. | |
| 2008/0006279 A1 | 1/2008 | Bodenham et al. | |
| 2008/0023013 A1 | 1/2008 | Tuke et al. | |
| 2008/0047567 A1 | 2/2008 | Bonutti | 128/852 |
| 2009/0277460 A1* | 11/2009 | Carrez | A61B 19/08 128/853 |
| 2009/0320177 A1 | 12/2009 | Lin et al. | |
| 2010/0031966 A1 | 2/2010 | Allen | |
| 2010/0138975 A1 | 6/2010 | Jordan et al. | |
| 2010/0299805 A1 | 12/2010 | Graneto, III | |
| 2010/0300459 A1 | 12/2010 | Lair | |
| 2011/0030703 A1 | 2/2011 | Chua | |
| 2011/0038792 A1 | 2/2011 | Xing | |
| 2011/0315150 A1 | 12/2011 | Bream, Jr. | |
| 2012/0167896 A1 | 7/2012 | Hartmann et al. | |
| 2012/0298115 A1 | 11/2012 | Haines et al. | |
| 2012/0298116 A1 | 11/2012 | Haines et al. | |
| 2012/0312308 A1 | 12/2012 | Allen | |
| 2013/0091615 A1 | 4/2013 | Pasko et al. | |
| 2013/0276204 A1 | 10/2013 | Pasko et al. | |

FOREIGN PATENT DOCUMENTS

| | | | |
|---|---|---|---|
| EP | 1066770 A1 | 1/2001 | |
| WO | WO 99/04721 A1 | 2/1999 | A61B 19/08 |
| WO | WO2007/083032 | 7/2007 | |

OTHER PUBLICATIONS

3M Technical Information Sheet, Product No. 1521, Feb. 2007 (2 pages).
3M Product Clinical Data Summary for No. 1521, 3M Plastic Medical Tape, Jan. 1996 (2 pages).
Medical Single Coated Film Tapes Selection Guide—Polyolefin & Vinyl, Nov. 1996 (3 pages).
Description and Photographs of D-09875-001 Snap Drape (as of Oct. 6, 2008) (1 page).
Description and Photographs of 75-1040 Fenestrated Snap Drape (as of Oct. 6, 2008) (1 page).
Description and Photographs of Perforated Drapes (as of Oct. 6, 2008) (2 pages).
Description and Photographs of a Perforated Drape With Tear Line (as of Oct. 6, 2008) (1 page).

(56) References Cited

OTHER PUBLICATIONS

European Search Report for European Application No. 09167307.9 dated Oct. 11, 2010 (5 pages).
International Search Report, International Application No. PCT/US2012/032122, dated Nov. 1, 2012, (3 pages).
International Search Report, International Application No. PCT/US2012/052079, dated Dec. 26, 2012, (3 pages).
International Search Report, International Application No. PCT/US2012/054659, dated Feb. 26, 2013, (3 pages).

* cited by examiner

ZIP STRIP DRAPING SYSTEM AND METHODS OF MANUFACTURING SAME

FIELD OF THE INVENTION

This invention relates to medical drapes, and more specifically to a medical drape system having a tearing feature for easy and clean removal of the drape from a patient.

BACKGROUND OF THE INVENTION

Medical drapes are widely used during the performance of surgical and other medical procedures as a protective measure. Medical drapes may be used to cover a patient during surgical or other medical procedures. Medical drapes are made sterile and are intended to prevent the possibility of infection being transmitted to the patient. Medical drapes provide protection to the patient by creating a sterile environment surrounding the surgical site and maintaining an effective barrier that minimizes the passage of microorganisms between non-sterile and sterile areas. To perform adequately, the drape should be made of a material that is resistant to blood, plasma, serums, and/or other bodily fluids to prohibit such fluids from contaminating the sterile field.

Medical drapes may, for example, be manufactured for use in connection with catheters such as central venous catheters (CVCs). CVCs may be used, for example, for intravenous drug therapy and/or parenteral nutrition. If the catheter or area surrounding the catheter becomes contaminated during or after being inserted into a patient, complications such as catheter site infection, suppurative phlebitis, and/or septicemia may result.

To minimize the risk of infection associated with catheterization, medical drapes often include fenestrations, or apertures, that extend completely through the drape to provide access to an adjacent area of the patient's body (for example, the subclavian area, the brachial area, or the femoral area) over which the respective fenestration lies. Because of the open nature of the fenestrations, a catheter may be inserted through the fenestrations and into the area of the patient's body adjacent to the fenestrations.

It has been generally problematic to remove the medical drape after the medical or surgical procedure is completed. For example, to remove the medical drape, scissors have been used to cut the medical drape from an exterior edge to a fenestration. The use of scissors near the site of the medical or surgical procedure and near the patient is not only awkward and, often, messy, but it is likely to cause injury to the patient or to the user, and can cause damage by cutting catheter or intravenous (IV) lines.

Some current medical drapes include perforations that pass completely through the drape and that form a weakened line, also referred to as a scoreline. To remove the drape, the user pulls the drape apart by hand without the use of any tools, such as scissors. However, one problem associated with this type of scoreline is that the sterile field is reduced because microorganisms can easily pass through the perforations.

Another problem associated with this type of medical drape is that, in general, the scorelines do not allow an easy or clean tear. For example, the tearing motion may require numerous attempts to initiate and complete the tear; the tearing motion may result in a tear-line that is different than the scoreline; and/or the tearing motion may encounter too much material resistance to complete the tear. A scoreline that does not easily tear can lead to frustration of the user, who is likely to continuously pull on the medical drape with a larger and unnecessary force. This, in turn, can lead to contaminants breaching the sterile field and, possibly, to other injuries or damage. For example, constant pulling on the medical drape can cause expensive medical instruments to fall down, or can cause sharp medical instruments to injure other staff, the patient, or the user. Additionally, the pulling involved with the larger and unnecessary force may cause discomfort to the patient who is the recipient of the larger and unnecessary force.

Other current medical drapes include an adhesive tape strip positioned along the length of a drape cut to overlap two adjacent sides of the drape cut. The adhesive tape strip is securely fixed to one side of the drape cut and is removably attached to the other (adjacent) side of the drape cut.

Similar to the medical drapes having scorelines, this type of medical drape fails to provide an easy and clean tear. The removably attached side of the adhesive tape strip often encounters resistance that interferes with easy removal of the medical drape. Furthermore, inadvertent pulling on the medical drape during or before the medical procedure can cause gaps between the removably attached side of the adhesive tape strip and the side of the drape cut to which it is attached. As such, the potential for contaminating the sterile field is greatly increased. Moreover, this type of medical drape involves additional manufacturing steps and costs, such as including a first layer of a permanent adhesive (on the fixed side of the adhesive tape strip) and a second layer of a removable adhesive (on the removable side of the adhesive tape strip).

Thus, it would be desirable to have a medical drape that assists in addressing one or more of the above problems.

SUMMARY OF THE INVENTION

According to one embodiment, a medical drape has a tool-less removal feature and includes a drape material, a drape cut, an adhesive tape strip, and a scoreline. The drape material has a top side, a back side, and at least one exterior edge. The drape cut has a starting point at the exterior edge and extends completely through the thickness of the drape material. The adhesive tape strip is positioned along the length of the drape cut to overlap at least a portion of the drape material on both sides of the drape cut to initially secure the two adjoining cut edges to each other. The scoreline extends along the length of the adhesive tape strip and only partially through the thickness of the adhesive tape strip to permit easy tearing of the adhesive tape strip for separation of the two adjoining cut edges.

According to another embodiment, a method for manufacturing an easily tearable medical drape includes providing a drape material having a top surface and a back surface, the back surface being positioned in contact with a patient when the medical drape is in use, the drape material having at least one exterior edge. The drape material is completely severed to form a drape cut extending from the exterior edge of the drape material to at least an inner area of the drape material, the drape cut being defined by two adjacent cut edges. The two adjacent cut edges are secured to each other by positioning an adhesive strip overlappingly with the drape cut, the adhesive strip extending over a portion of each of the two adjacent cut edges. The adhesive strip is partially severed through its thickness to form a strip scoreline extending along a length of the adhesive strip, the strip scoreline overlapping the drape cut to permit easy tearing of the adhesive strip for separation of the two adjoining cut edges.

According to yet another embodiment, a method for manufacturing a medical drape includes providing a sheet having at least one layer of drape material, and severing the sheet completely through its thickness from an outer edge of the sheet to an inner area of the sheet to form a sheet cut. The sheet cut separates a first sheet area from an adjacent second sheet area. A strip is provided for securing the first sheet area to the second sheet area. The strip is partially severed through its thickness to form a strip scoreline, the strip scoreline separating a first strip area and an adjacent second strip area. A portion of the first strip area is fixed to a portion of the first sheet area and a portion of the second strip area to a portion of the second sheet area such that the strip scoreline is in an overlapping position with respect to the sheet cut.

The above summary of the present invention is not intended to represent each embodiment or every aspect of the present invention. The detailed description and Figures will describe many of the embodiments and aspects of the present invention.

BRIEF DESCRIPTION OF DRAWINGS

The foregoing and other advantages of the invention will become apparent upon reading the following detailed description and upon reference to the drawings.

While the invention is susceptible to various modifications and alternative forms, specific embodiments are shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF THE PREFERRED EMBODIMENTS

In surgical procedures, many times intravenous (IV) lines or other delivery or drainage lines must remain in the patient after the procedure is complete. Described below in more detail is a medical system for removing a medical or surgical drape after completing a medical or surgical procedure without dislodging any remaining lines. The medical system includes features directed to manually tearing apart the medical drape, by hand, without using any tools (e.g., scissors). An advantage of the medical system is that it eliminates the potential for injury or damage caused by the tools. Another advantage of the medical system is that it consistently provides a clean and smooth tear in the medical drape. A further advantage of the medical system is that the tearing can be easily accomplished with the exertion of little force. Yet another advantage of the medical system is that it eliminates the potential for contamination of a sterile field, by adequately sealing adjoining edges of a drape cut in the medical drape.

Figure 1:
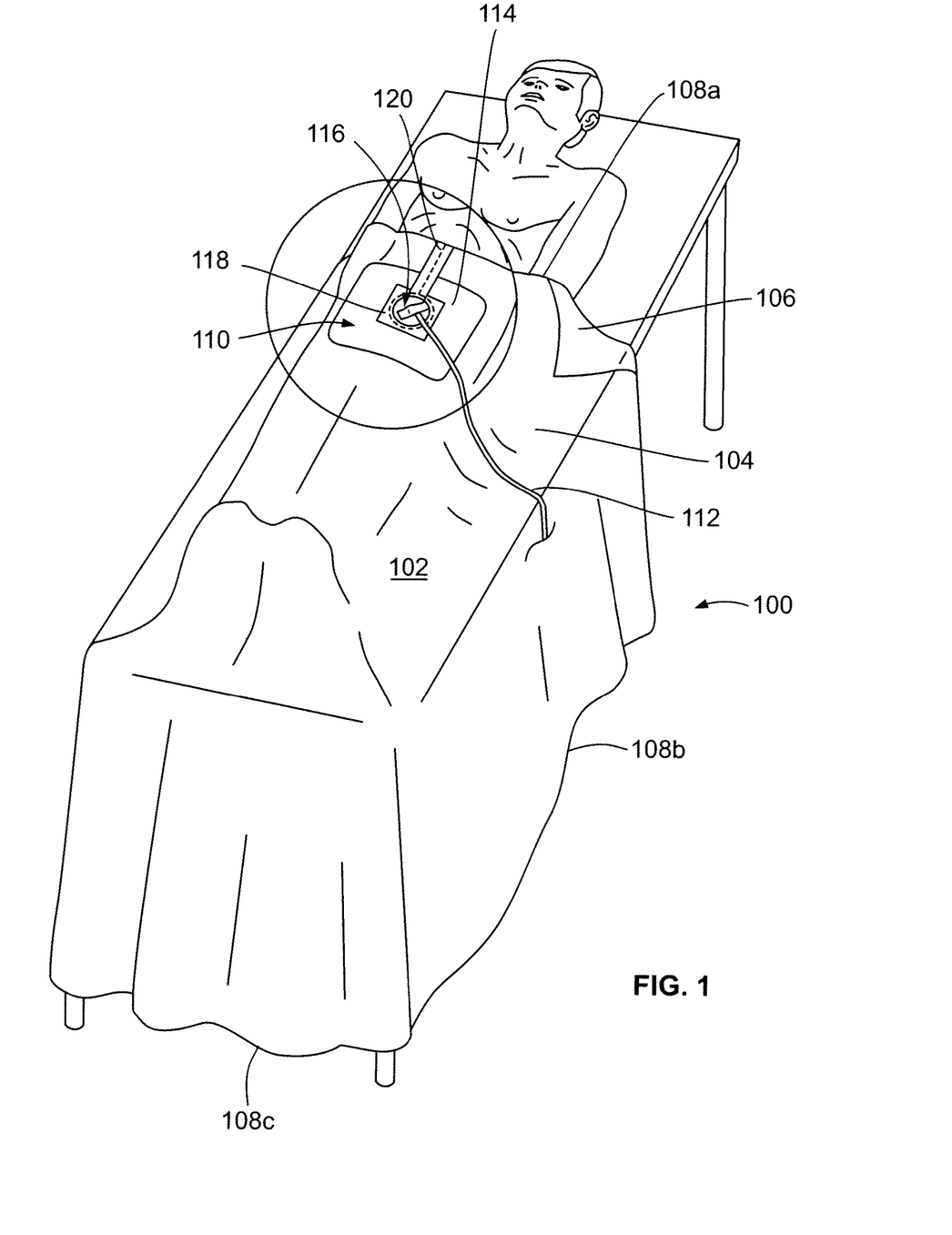
FIG. 1 is a perspective view illustrating a medical drape in a medical procedure, according to one embodiment.

Referring to FIG. 1, a medical drape 100 according to one embodiment of the medical system is illustrated generally as it would appear after being unfolded and ready for use in a surgical or medical procedure (for example, catheterization, angiography, and radiology). The drape 100 is generally a single use disposable drape and includes a main drape material 102 and has dimensions suitable for covering the patient's entire body, including, in some embodiments, the patient's head and face to assist in maintaining the sterility of the surgical area and thereby lower the risk of infection. In such embodiments, the total length of the drape 100 generally ranges from about 115 in. to about 125 in. (about 292 cm to about 318 cm). In other embodiments, the drape 100 may cover less than the patient's entire body and may have a length ranging generally from about 24 in. to about 150 in. (about 61 cm to about 381 in). The total width of the drape 10 generally ranges from about 24 in. to about 80 in. (about 61 cm to about 204 cm).

The drape 100 has a front side 104, which faces away from a patient when in use, and a back side 106, which contacts the patient when in use. The drape 100 includes a plurality of exterior edges 108a-108c. The main drape material 102 is generally made of a water-repellent or water-impermeable material and/or is coated with such a water-repellent or water impermeable material to prevent the passage of bodily fluids and/or contaminating microorganisms. For example, the main drape material 102 can include various woven, non-woven, hydroentangled materials, and/or combinations thereof. The base fabrics used in the main drape material 102 may include absorbent Airlaid, spunlace, blends of polyester, polypropylene, polyethylene, urethane, and/or combinations thereof. The drape material 102 may be manufactured using various methods, including a spunbond metblown spundbond (SMS) method, a spunbond metblown metblown spundbond method (SMMS), and a spunbond metblown metblown metblown spundbond method (SMMMS). In alternative embodiments, one or more antimicrobial layers are added to further enhance antimicrobial protection. For example, an antimicrobial coating can be sprayed on the front side 104 and/or the back side 106 of the drape 100.

A fenestration 110 is optionally positioned on and extends completely through the thickness of the main drape material 102. The fenestration 110 allows for a surgical or other medical procedures to be performed therethrough. For example, a catheter tube 112 can be attached directly to the patient through the fenestration 110. In alternative embodiments, additional fenestrations can be positioned on the main drape material 102 and in any suitable location on the main drape material 102. Furthermore, although the fenestration 110 has been illustrated to be generally rectangular in the described embodiment, in alternative embodiments the fenestration(s) can be generally circular, egg-shaped, oval-shaped, pear-shaped, football-shaped, or the like. It is further contemplated that the drape may have any of the properties described herein, regardless of the shape, number, and/or location of the fenestrations.

The fenestration 110 may be covered at least in part with an adhesive incise film 114. The composition of the incise film 114 is well known to those skilled in the art of medical drapes. One example of an incise film that may be used is OpSite® Incise film manufactured by Smith & Nephew, Inc. (Memphis, Tenn.). The incise film 114 may be generally transparent so that the health care provider may have clear visibility for locating the correct position for inserting the catheter 112 or otherwise accessing the patient site. The incise film 114 may be positioned on the front side 104 or on the back side 106 of the drape 100, so long as an exposed adhesive side of the incise film 114 faces toward the patient. The incise film 114 is intended to be removably fixed to the patient, e.g., by attaching the adhesive side to the patient, during the procedure. As such, removal of the drape 100 from the patient may be difficult to accomplish without exerting tugging and/or pulling on the drape 100 (and, consequently, on the patient), unless removal features are included in the drape 100 to facilitate easy tearing.

The incise film 114 includes, optionally, an access port 116 being positioned on and extending completely through the incise film 114. The access port 116 allows the catheter tube 112 to be readily inserted without any cutting, puncturing, or further modification of the drape 100 or incise film 114. Although the access port 116 of the illustrated embodiment is circular, it is contemplated that other general shapes including, but not limited to, rectangles, other polygons, circles, and ovals may be used. The access port 116 may have an area ranging from about 3 in$^2$ to about 5 in$^2$ (about 19 cm$^2$ to about 33 cm$^2$). Optionally, additional access ports can be included.

The exposed adhesive side of the incise film 114 is generally covered by at least one release liner 118, which is located on the back side 106 of the main drape material 102. Although the release liner 118 is generally removed when the drape 100 is placed over the patient, the release liner 118 of FIG. 1 is shown for illustration purposes. The release liner 118 may be one continuous piece of liner, strips, or the like. When the release liner 118 is removed, the adhesive side of the incise film 114 may be coupled to the patient to keep the drape 100 and, in particular, the fenestration 110 in place during the procedure.

An adhesive tape strip (or zip strip) 120 is positioned on the main drape material 102, extending from a top exterior edge 108a of the drape 100 internally to the access port 116. For example, the adhesive tape strip 120 is glued to the front side 104 of the main drape material 102. Optionally, the adhesive tape strip 120 is glued to the back side 106. In alternative embodiments, the adhesive tape strip 120 extends from any exterior edge 108a-108c to any internal area of the main drape material 102 or to another exterior edge 108a-108c. Any number of adhesive tape strips 120 can be included in the drape 100 in any orientation.

According to one embodiment, the adhesive tape strip 120 is a single-coated polyethylene medical tape, such as a medical tape manufactured by 3M (St. Paul, Minn.) as product number 1521. The 3M Medical Tape 1521 is a single-coated tape having a matte finish which includes a transparent polyethylene and is coated with a hypoallergenic, pressure sensitive acrylate adhesive and includes a liner that is silicone treated and is polyethylene coated on one side only along with a bleached Kraft paper release liner. The 3M medical tape has a tape caliper of 6.4 mil (0.16 mm) of polyethylene film tape, a backing of 5.0 mil (0.13 mm) translucent polyethylene film, an acrylate adhesive (designed for medical/surgical use), and a release liner of 83 lb poly-coated Kraft paper, with silicone on one side (6 mils/ 0.15 mm). The adhesion to steel of the 3M Medical Tape 1521 is 21 ounces/inch width (0.6 kg/25 mm width). Other suitable medical tapes manufactured by 3M and/or other manufacturers may be used in connection with the adhesive tape strip 120.

Figure 2A:
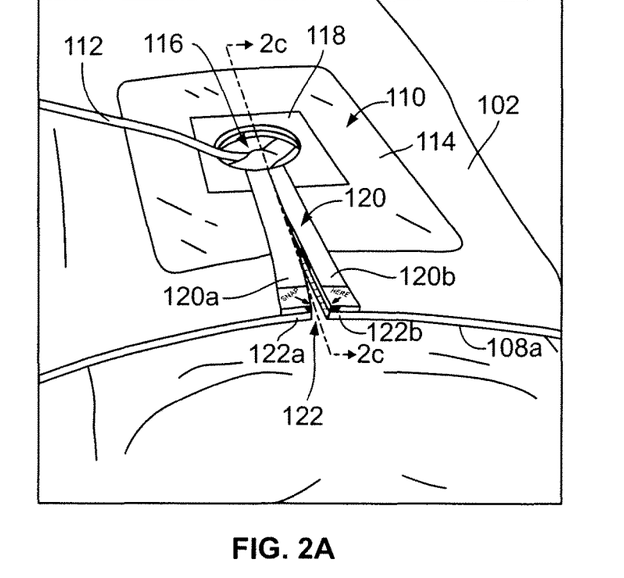
FIG. 2A is an enlarged perspective view illustrating an adhesive tape strip having a scoreline and being attached to the medical drape of FIG. 1.
Figure 2B:
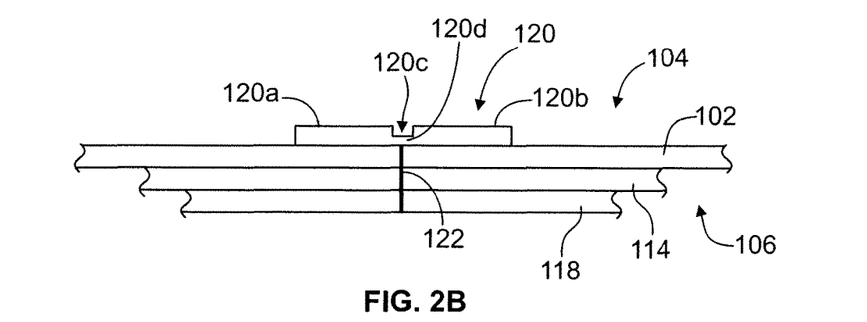
FIG. 2B is, generally, a front view of FIG. 2A illustrating the depth of the scoreline through the thickness of the adhesive tape strip.
Figure 2C:
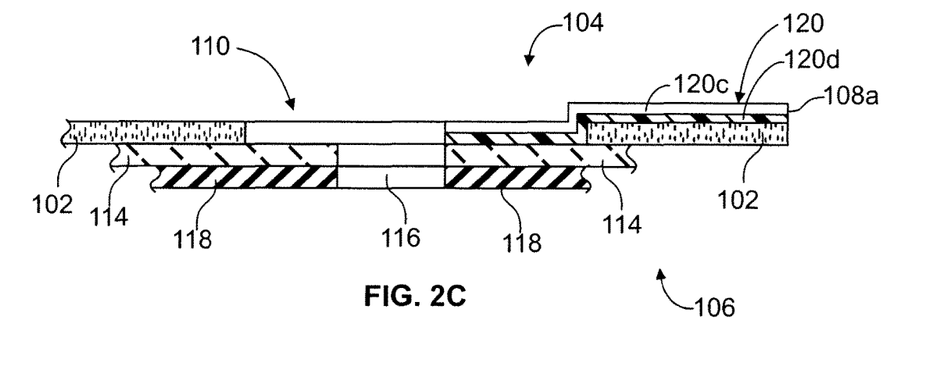
FIG. 2C is, generally, a cross-sectional side view of FIG. 2A illustrating the depth of the scoreline along the length of the adhesive tape strip.

Referring to FIGS. 2A-2C, the adhesive tape strip 120 generally includes a first strip side 120a and a second strip side 120b, which are connected along a strip scoreline 120c via a bridging area 120d. The strip scoreline 120c is generally formed by severing the adhesive tape strip 120 along its length partially through its thickness such that a separated area is formed above the bridging area 120d between the first strip side 120a and the second strip side 120b. Thus, based at least in part on the relatively small thickness of the bridging area 120d, the first strip side 120a can be easily separated from the second strip side 120b. Also, the adhesive tape strip 120 can be easily separated from the main drape material 102 by selecting an appropriate removable adhesive material when fixing the adhesive tape strip 120 to the main drape material 102. In this exemplary embodiment, the strip scoreline 120c is generally centrally positioned along the width (i.e., narrow dimension) of the adhesive tape strip 120.

The adhesive tape strip 120 is positioned such that the strip scoreline 120c overlaps a drape cut 122 of the drape 100. The drape cut 122 is formed by completely severing the main drape material 102, the incise film 114, and the liner 118, from the top exterior edge 108a through the access port 116. The drape cut 122 is generally defined by two adjoining cut edges, a first cut edge 122a and a second cut edge 122b. The adhesive tape strip 120 secures the adjoining first and second cut edges 122a, 122b of the drape cut 122 to each other by having the first strip side 120a fixed (e.g., glued) to the a first cut edge 122a and having the second strip side 120b fixed to the second cut edge 122b. The bridging area 120d is the only material that holds together the first and second cut edges 122a, 122b.

In addition to securing the drape cut 122, the adhesive tape strip 120 seals the drape cut 122 to eliminate any violation of a sterile field formed on the patient side. Because the strip scoreline 120c extends only through part of the thickness of the adhesive tape strip 120, a protective barrier—the bridging area 120d—is inherently present during the medical procedure.

Figure 3:
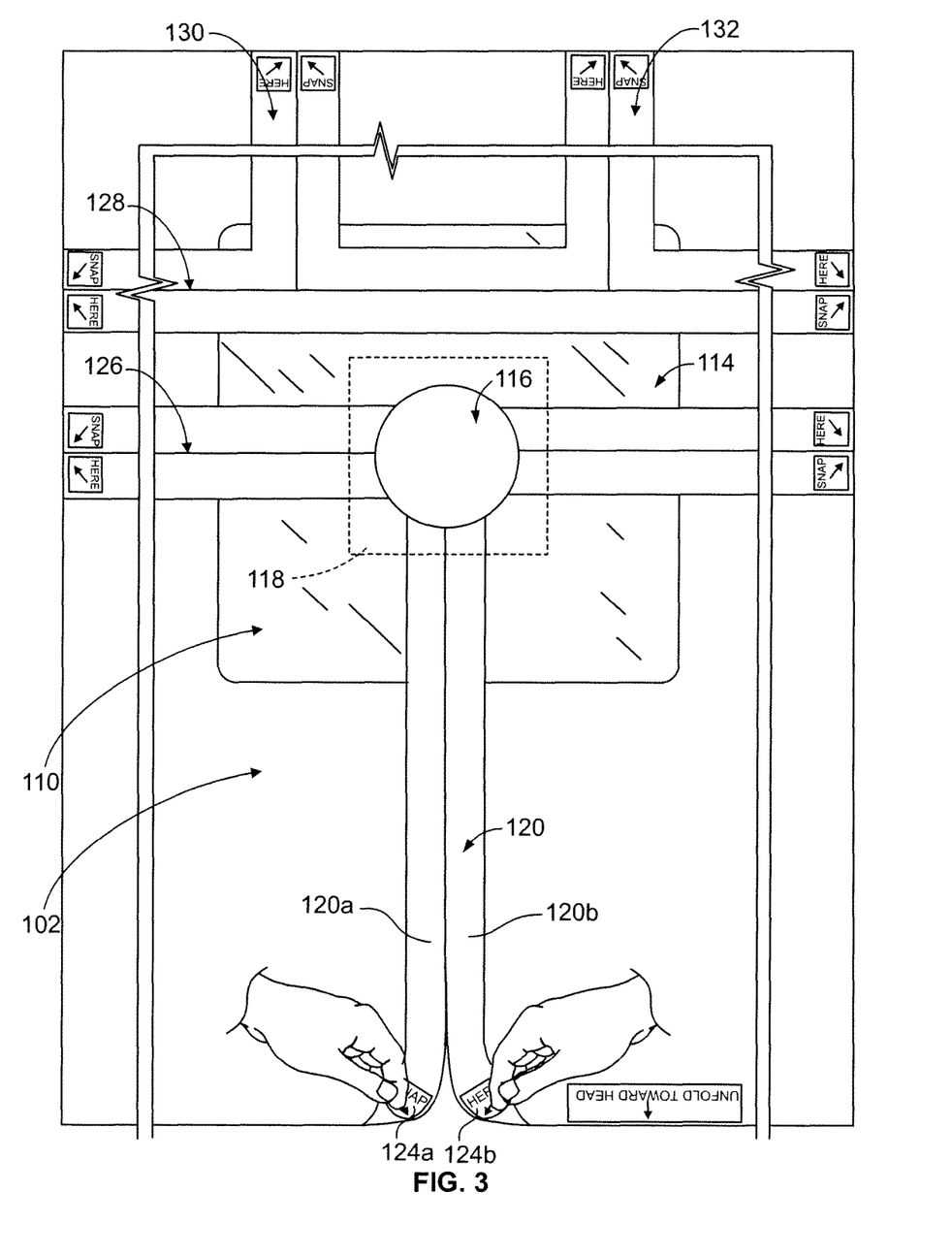
FIG. 3 is a perspective view illustrating the act of tearing of the adhesive tape strip.

Referring to FIG. 3, the drape 100 is easily removed after the medical or surgical procedure is completed. A staff person pulls apart two indicators 124a, 124b, which may be generally indicated as "Tear Here" or "Snap Here," of the drape 100 to tear apart the adhesive tape strip 120 along the scoreline 120c. The first and second strip sides 120a, 120b are simply pulled apart as the material of the bridging area 120d is being torn. Because, the drape cut 122 is a complete sever of the materials associated with the main drape material 102, the incise film 114, and the liner 118, these materials provide no resistance to the act of tearing, i.e., they are pre-cut. Consequently, the tearing of the adhesive tape strip 120 provides a smooth and clean tear. As a further advantage, the tearing of the adhesive tape strip 120 can be easily accomplished with the exertion of little force that renders the drape system simple for use from both the user's and the patient's perspective.

Optionally, one or more additional adhesive tape strips 126, 128, 130, 132 can be positioned on the drape material 102. The adhesive tape strips 126, 128, 130, 132 can be positioned and oriented in any location, can extend from any area to any other area of the drape material 102, and can be of any suitable number.

Figure 4:
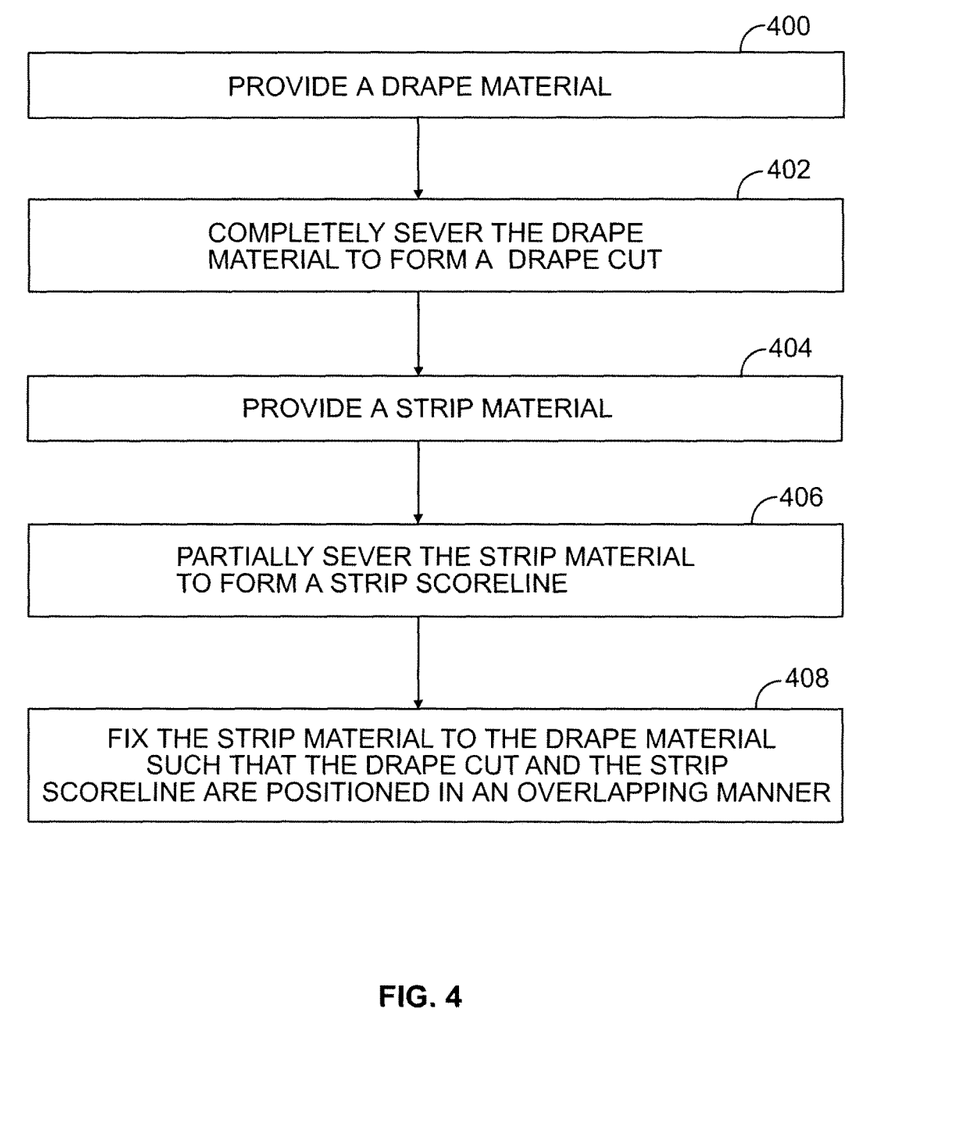
FIG. 4 is a flowchart illustrating a method for making the medical drape of FIG. 1, according to an alternative embodiment.

Referring to FIG. 4, a method of manufacturing the drape 100 includes providing a drape material (400) and completely severing the drape material to form a drape cut (402). A strip material is provided (404) and a partial sever of the strip material is made to form a strip scoreline (406). The strip material, for example, can have a thickness of about 0.2 inches (about 5 mm), a width of about 1.5 inches (about 38 mm) to about 3 inches (about 76 mm), and can extend from about 35% to about 60% through the thickness of the strip material (e.g., about 0.07 inches to about 0.12 inches, or about 1.8 mm to about 3 mm). The strip material is fixed to the drape material such that the drape cut and the strip scoreline are positioned in an overlapping manner (408).

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention, which is set forth in the following claims.

What is claimed is:

1. A medical drape having a tool-less removal feature, the medical drape comprising:
   a drape material having a top side and a back side, the back side capable of being positioned in contact with a patient when the medical drape is in use, the drape material having at least one exterior edge;
   a drape cut having a starting point at the at least one exterior edge, the drape cut extending completely through a thickness of the drape material such that two adjoining cut edges are completely severed from one another to permit easy separation of the two adjoining cut edges;
   an adhesive tape strip positioned along an entire length of the drape cut, the adhesive tape strip adhered to and overlapping at least a portion of the drape material on both sides of the drape cut to initially secure the two adjoining cut edges to each other to eliminate violation of a sterile field, the adhesive tape strip including a bridging area adjacent the drape cut and a separated area formed above the bridging area between a first strip side and a second strip side, the bridging area securing the adjoining cut edges of the drape material and having a smaller thickness than the adhesive tape strip; and
   a scoreline formed partially through a thickness of the adhesive tape strip and extending along a length of the adhesive tape strip to permit easy tearing of the adhesive tape strip for separation of the two adjoining cut edges, wherein the scoreline is generally centrally positioned along a width of the adhesive tape strip.

2. The medical drape of claim 1, wherein the scoreline extends from 35% to 60% through the thickness of the adhesive tape strip.

3. The medical drape of claim 1, wherein the adhesive tape strip is a film having a thickness of 0.2 inches and a width from 1.5 inches to 3 inches.

4. The medical drape of claim 1, wherein the adhesive tape strip is positioned on one of the top side of the drape material and the back side of the drape material.

5. The medical drape of claim 1, further comprising at least one indicator for indicating the starting point of the drape cut.

6. The medical drape of claim 1, further comprising at least one fenestration located on the drape material, the at least one fenestration extending completely through a thickness of the drape material to expose a patient area when the medical drape is in use, the drape cut having an ending point at the at least one fenestration.

7. The medical drape of claim 1, wherein the drape cut has an ending point at another said at least one exterior edge, the drape cut extending along its length from the starting point to the ending point.

8. The medical drape of claim 1, wherein the drape material includes one or more of a water repellent material, a water-impermeable material, a coating of water-repellent material, a coating of water-impermeable material, a woven material, a non-woven material, a hydroentangled material, a spunlace material, a polyester material, a polyethylene material, a polypropylene material, a urethane material, a spunbond meltblown spunbond material, a spunbond meltblown meltblown spunbond material, a spunbond meltblown meltblown meltblown spunbond material, and combinations thereof.

9. The medical drape of claim 1, further comprising at least one additional layer of material, the at least one additional layer being attached to one of the top side and the back side of the drape material, the drape cut extending completely through a thickness of the at least one additional layer.

* * * * *